US010012592B2

(12) United States Patent
Abate et al.

(10) Patent No.: US 10,012,592 B2
(45) Date of Patent: Jul. 3, 2018

(54) MANAGING VARIATION IN SPECTROSCOPIC INTENSITY MEASUREMENTS THROUGH THE USE OF A REFERENCE COMPONENT

(71) Applicant: Bio-Rad Laboratories, Inc., Hercules, CA (US)

(72) Inventors: Adam Abate, Cambridge, MA (US); John Lawrence Emhoff, Cambridge, MA (US); Tony Hung, Cambridge, MA (US); Adnan Moez Esmail, Cambridge, MA (US); Sepehr Kiani, Cambridge, MA (US); Pascaline Mary, Cambridge, MA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 15/722,486

(22) Filed: Oct. 2, 2017

(65) Prior Publication Data

US 2018/0045648 A1 Feb. 15, 2018

Related U.S. Application Data

(63) Continuation of application No. 14/008,990, filed as application No. PCT/US2012/030909 on Mar. 28, 2012, now Pat. No. 9,816,931.

(Continued)

(51) Int. Cl.
*G01J 1/10* (2006.01)
*G01J 3/30* (2006.01)
(Continued)

(52) U.S. Cl.
CPC ....... *G01N 21/6486* (2013.01); *C12Q 1/6806* (2013.01); *G01N 21/255* (2013.01);
(Continued)

(58) Field of Classification Search
CPC ............ G01B 11/002; G01N 21/6486; G01N 21/255; G01N 21/76; G01N 2201/06113; G01N 2201/062; C12Q 1/6808
(Continued)

(56) References Cited

U.S. PATENT DOCUMENTS

| 5,723,345 A | 3/1998 | Yamauchi et al. |
| 6,391,562 B2 | 5/2002 | Kambara et al. |

(Continued)

FOREIGN PATENT DOCUMENTS

| EP | 1912067 | 4/2008 |
| EP | 2364774 A2 | 9/2011 |

(Continued)

OTHER PUBLICATIONS

International Search Report and Written Opinion from PCT/US2012/030909, dated Jul. 16, 2012.

(Continued)

*Primary Examiner* — Hina F Ayub
(74) *Attorney, Agent, or Firm* — Kilpatrick Townsend and Stockton LLP (57) ABSTRACT

The present invention generally pertains to methods and kits for managing the variation in spectroscopic intensity measurements through the use of a reference component. The reference component may comprise a reference spectroscopic substance and may be contained together with a sample of interest in a sample to be tested, wherein the sample of interest may comprise a sample spectroscopic substance. Each sample to be tested may be uniquely identified and, hence, "barcoded" by combinations of different colors and concentrations of spectroscopic substances, contained therein.

9 Claims, 8 Drawing Sheets

Related U.S. Application Data (60) Provisional application No. 61/469,900, filed on Mar. 31, 2011.

(51) Int. Cl.
  *G01N 21/64* (2006.01)
  *G01N 21/76* (2006.01)
  *G01N 21/25* (2006.01)
  *C12Q 1/6806* (2018.01)

(52) U.S. Cl.
  CPC ....... *G01N 21/76* (2013.01); *G01N 2201/062* (2013.01); *G01N 2201/06113* (2013.01)

(58) Field of Classification Search
  USPC .................................... 356/620, 306, 243.1
  See application file for complete search history.

(56) References Cited

U.S. PATENT DOCUMENTS

| | | |
|---|---|---|
| 8,528,589 B2 | 9/2013 | Miller et al. |
| 8,535,889 B2 | 9/2013 | Larson et al. |
| 9,555,411 B2 | 1/2017 | Kiani et al. |
| 2005/0095649 A1 | 5/2005 | Aebersold |
| 2005/0143943 A1 | 6/2005 | Brown |
| 2005/0161669 A1 | 7/2005 | Jovanovich et al. |
| 2008/0037006 A1 | 2/2008 | Triana et al. |
| 2011/0151578 A1 | 6/2011 | Abate et al. |
| 2011/0218123 A1 | 9/2011 | Weitz et al. |
| 2011/0250597 A1 | 10/2011 | Larson et al. |
| 2011/0267457 A1 | 11/2011 | Weitz et al. |
| 2012/0015822 A1 | 1/2012 | Weitz et al. |
| 2012/0132288 A1 | 5/2012 | Weitz et al. |
| 2012/0219947 A1 | 8/2012 | Yurkovetsky et al. |
| 2012/0220494 A1 | 8/2012 | Samuels et al. |
| 2012/0222748 A1 | 9/2012 | Weitz et al. |
| 2012/0309002 A1 | 12/2012 | Link |
| 2014/0354795 A1 | 12/2014 | Tracy et al. |
| 2015/0024945 A1 | 1/2015 | Healy |
| 2015/0065396 A1 | 3/2015 | Kiani et al. |

FOREIGN PATENT DOCUMENTS

| | | |
|---|---|---|
| EP | 2662135 A2 | 11/2013 |
| WO | 2007/081385 A2 | 7/2007 |
| WO | 2007/081387 A1 | 7/2007 |
| WO | 2009/085215 A1 | 7/2009 |
| WO | 2012/078710 A1 | 6/2012 |
| WO | 2012/135201 A1 | 10/2012 |
| WO | 2012/135259 A1 | 10/2012 |
| WO | 2013/095737 A2 | 6/2013 |
| WO | 2013/122826 A1 | 8/2013 |
| WO | 2013/165748 A1 | 11/2013 |
| WO | 2014/043388 A1 | 3/2014 |
| WO | 2014/093976 A1 | 6/2014 |
| WO | 2014/117088 A1 | 7/2014 |
| WO | 2014/176599 A1 | 10/2014 |

OTHER PUBLICATIONS

Altria et al., "Improved performance in capillary electrophoresis using internal standards", internet Citation, Apr. 18, 2012, pp. 1-5.

Brouzes et al., "Droplet microfluidic technology for single-cell high-throughput screening", Proceedings of the National Academy of Sciences of the United States of America, vol. 106, No. 34, Aug. 25, 2006, pp. 14195-14200.

EP12764041.5 , "Extended European Search Report", dated Dec. 16, 2013, 7 pages.

EP16151499.7 , "Extended European Search Report", dated Jun. 16, 2016, 6 pages.

Lee et al., "Seven-color, homogeneous detection of six PCR products", Biotechniques, vol. 27, No. 2 Informa Healthcare, Aug. 1, 1999, pp. 342-349.

Newkirk et al., "Determination of genomic copy number with quantitative microsphere hybridization", Human Mutation, John Wiley & sons, INC, US, vol. 27, No. 4, Apr. 1, 2006, pp. 376-386.

Srisa-Art, M. et al., "High-Throughput DNA Droplet Assays Using Picoliter Reactor Volumes"; Analytical Chemistry; vol. 79, No. 17; Sep. 1, 2007; pp. 6682-6689.

MANAGING VARIATION IN SPECTROSCOPIC INTENSITY MEASUREMENTS THROUGH THE USE OF A REFERENCE COMPONENT

RELATED APPLICATIONS AND INCORPORATION BY REFERENCE

This application is a continuation of U.S. patent application Ser. No. 14/008,990, filed on Oct. 15, 2014, which is a national phase application under 35 USC § 371 of PCT Application No. PCT/US2012/030909 filed Mar. 28, 2012, which claims the benefit of priority to U.S. provisional patent application Ser. No. 61/469,900 filed Mar. 31, 2011, the teaching and contents of each of which are hereby incorporated by reference for all purposes.

The foregoing application, and all documents cited therein or during its prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention is in the technical field of analytical chemistry. More particularly, the present invention relates to spectroscopy as applied to microfluidics.

BACKGROUND OF THE INVENTION

Microfluidic processes often employ detection methods involve determining spectroscopic properties of light from a sample, where the light may be scattered from a sample, or emitted as chemiluminescence by a chemical process within a sample, or transmitted through a sample, or selectively absorbed by a sample, or emitted as fluorescence from a sample following excitation. The outcomes of the spectroscopic assays can then be determined by running the samples past an optical detector to measure the optical intensities. For example, samples that yield relatively high fluorescence intensity may be interpreted as having a large concentration of fluorescently-labeled material, whereas relatively dim droplets may be interpreted as having a low concentration of fluorescently-labeled material. This allows information about the efficiency of the reaction to be inferred based upon the optical intensity detected.

However, such measurements can be sensitive to noise such that two samples with identical content in fluorescent dyes, as in the case of fluorescence-based assays, may be classified differently due to variations in measurements, making the analysis difficult and inaccurate. This can result from imperfection in the microfluidic processing of the samples but can also be due to electronic and optical noise, changes in environmental conditions, or any combination of the above. Accordingly, there is a need for a technique to manage the variation in spectroscopic intensity measurements.

The present invention provides a method for managing variation in spectroscopic intensity measurements through the use of a reference component.

Citation or identification of any document in this application is not an admission that such document is available as prior art to the present invention.

SUMMARY OF THE INVENTION

The present invention generally pertains to a method for managing variation in spectroscopic intensity measurements through the use of a reference component. One embodiment of the method of the present invention may comprise a sample of interest (sample) and a reference component, which together may comprise a sample to be tested. The reference component and the sample of interest may each further comprise a molecule having known and expected spectroscopic properties, referred to as a "reference spectroscopic substance" and a "sample spectroscopic substance", respectively. In one aspect of this embodiment, the sample of interest may comprise one or more sample spectroscopic substances. Depending upon the application, the spectroscopic substance may comprise one or more light-scattering molecule, chemiluminescent molecule, selectively absorbent molecule, or fluorescent molecule. In one aspect of this embodiment, the reference spectroscopic substance and the sample spectroscopic substance may be substantially distinct when present within the same sample to be tested. In another aspect of this embodiment, each sample to be tested may be uniquely identified and may be "barcoded" by combinations of different colors and concentrations of spectroscopic substances comprised therein.

In one aspect of this embodiment, the sample to be tested is present in a vehicle, wherein the vehicle may comprise a droplet; a bead or collection of beads; a fluid; or an emulsion. In one example of this aspect, the vehicle may comprise a collection of beads, wherein each bead in the collection may comprise a reference spectroscopic substance and sample spectroscopic substance, each of which may be identical to the respective spectroscopic substances on each bead in the same collection. In another aspect of this embodiment, the sample to be tested may be present within a vehicle in a microfluidic device.

According to the method of the present invention, the sample to be tested may be analyzed for spectroscopic intensity measurements of each spectroscopic substance, wherein the spectroscopic intensity measurement of the reference spectroscopic substance may be used to correct the spectroscopic intensity measurement of the one or more sample spectroscopic substances. Depending on the application, the spectroscopic properties may comprise: light scattered from a sample to be tested following illumination of the sample to be tested; light emitted as chemiluminescence by a chemical process within the sample to be tested; light selectively absorbed by a sample to be tested following direction of a broadband light source at the sample to be tested; or light emitted as fluorescence from a sample to be tested following excitation of the sample to be tested.

Another embodiment of the present invention pertains to a method for managing variation in spectroscopic intensity measurements through the use of a reference component as previously described, which may further comprise a library of samples to be tested, wherein the reference spectroscopic substance and the one or more sample spectroscopic substances may be substantially distinct when present within the same sample to be tested and, accordingly, each sample to be tested may be uniquely identified by the combination of different colors and concentrations of spectroscopic substances comprised therein. In one aspect of this embodiment, the library of samples to be tested may be analyzed for spectroscopic intensity measurements of each spectroscopic substance, wherein the spectroscopic intensity measurement of the reference spectroscopic substance may be used to correct the spectroscopic intensity measurement of the one or more sample spectroscopic substances. In another embodiment of the method of the present invention, the library of samples to be tested may be present within a microfluidic device.

Another embodiment of the present invention pertains to a method for reducing the variation in spectroscopic intensity measurements in a library of samples to be tested through the use of a reference component as previously described, wherein each sample to be tested in the library of samples to be tested further may comprise one or more probes, wherein each probe may comprise a DNA sequence, wherein each of the one or more sample spectroscopic substances may serve as a unique identifier for the identity of a particular probe within a particular sample to be tested, and wherein the reference spectroscopic substance and the one or more sample spectroscopic substances within a particular sample to be tested may be substantially distinct. In one aspect of this embodiment, each of the one or more probes may be substantially identical to each other when present within a single sample to be tested. In this embodiment, each sample to be tested may be uniquely identified by the combination of different colors and concentrations of spectroscopic substances comprised therein. In another aspect, each of the one or more probes may be substantially different from each other when present in separate samples to be tested. In one aspect of this embodiment, the library of samples to be tested may be analyzed for spectroscopic intensity measurements of each spectroscopic substance, wherein the spectroscopic intensity measurement of the reference spectroscopic substance may be used to correct the spectroscopic intensity measurement of the one or more sample spectroscopic substances. In another aspect, the identity of the one or more probes in each sample to be tested may be determined from the corrected spectroscopic intensity measurements of each sample spectroscopic substance. In another embodiment of the method of the present invention, the library of samples to be tested may be present within a microfluidic device.

Another embodiment of the present invention pertains to a method for managing variation in spectroscopic intensity measurements through the use of a reference component as previously described, which may further comprise an assay performed within a sample to be tested, and wherein the measured spectroscopic intensity may comprise a combination of the result(s) of the assay performed and the combination and concentration of spectroscopic substances within the sample to be tested. In one aspect of this embodiment, the concentration of the spectroscopic substances in the sample to be tested may be a result of adding the spectroscopic substances together, wherein the product of such addition may have variability that may result in undesired concentration variation. In another embodiment of the method of the present invention, the sample to be tested may be present within a microfluidic device.

The present invention also pertains to a kit containing the reagents necessary for performing methods for managing variation in spectroscopic intensity measurements through the use of a reference component, as described previously and further herein.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example but not intended to limit the invention solely to the specific embodiments described, may best be understood in conjunction with the accompanying drawings.

FIGS. 3A-D illustrate examples of one embodiment of a method for managing the variation in spectroscopic intensity measurements, specifically fluorescence intensity measurements by way of example, resulting from injection variability with a reference component comprising a fluorescent dye as a reference spectroscopic substance, according to the present invention.

DETAILED DESCRIPTION OF THE INVENTION

The present invention generally pertains to a method for managing variation in spectroscopic intensity measurements through the use of a reference component. One embodiment of the method of the present invention comprises a sample of interest and a reference component, which together may comprise a sample to be tested.

The "sample", as used in the term "sample spectroscopic substance", is further used interchangeably with the term "sample of interest". Both "sample" and "sample of interest", as used interchangeably herein, in singular or plural form and not intended to be limited to any particular quantity, mean a molecule or substance that the user wishes to gather information from for purpose of performing some test or assay.

A "sample to be tested", as used herein, means the sample (or sample of interest) together with a reference component. In one embodiment of the present invention, the sample to be tested is present within a vehicle. In another embodiment of the present invention, the sample to be tested is present within a vehicle in a microfluidic device.

The reference component and the sample of interest may each further comprise a substance having known and expected spectroscopic properties and present in any concentration, referred to as a "reference spectroscopic substance" and a "sample spectroscopic substance", respectively, collectively referred to as "spectroscopic substances", and individually referred to as "spectroscopic substance". In one aspect of this embodiment, the sample may comprise one or more sample spectroscopic substances. In another aspect of this embodiment, each sample to be tested is uniquely identified and, hence, "barcoded" by combinations of different colors and concentrations of spectroscopic substances comprised therein. Examples of spectroscopic substances are discussed further below.

In one embodiment of the present invention, the sample of interest may comprise one or more of the following: a single-phase flow, the composition of which may vary with time; a cell or microorganism or collection of cells or microorganisms (including any eukaryotic or prokaryotic cell or microorganism, including but not limited to those selected from humans, animals, plants, fungi, bacteria, viruses, protozoa, yeasts, molds, algae, rickettsia, and prions); proteins; peptides; nucleic acid sequences; oligonucleotide probes; or a chemical reaction comprising one or more reagent or reaction component, including but not limited to, organic and inorganic chemicals, enzymes (including polymerase enzymes), buffers, and dNTPs.

In one embodiment of the method of the present invention, the vehicle is a droplet. A "droplet", as used herein, means an isolated aqueous or lipophilic phase within a continuous phase having any shape, for example but not limited to, cylindrical, spherical and ellipsoidal, as well as flattened, stretched or irregular shapes and so on. One or more droplets according to the present invention may be used to perform various functions, including but not limited to, serving as reaction vessels for performing chemical reactions; collectively encompassing a library of elements, including but not limited to a library of oligonucleotide probes; or as lenses for focusing a laser for optical applications. In one embodiment of the invention, one or more droplets are contained within an emulsion. In another embodiment of the invention, one or more droplets are contained within an emulsion in a microfluidic device.

In another embodiment of the method of the present invention, the vehicle is a bead or a collection of beads. A "bead", as used herein, refers to a fine particle used as a substrate or matrix for reactive substances and/or identifying labels in a diagnostic application, including beads of magnetic material, silica, or polymers including, but not limited to, polystyrene. In one embodiment of the invention, one or more beads or a collection of beads are contained within an emulsion. In another embodiment of the invention, one or more beads or a collection of beads are contained within an emulsion in a microfluidic device.

In another embodiment of the method of the present invention, the vehicle is a fluid. A "fluid", as used herein, is any aqueous or lipophilic phase capable of flowing freely.

In another embodiment of the method of the present invention, the vehicle is an emulsion. An "emulsion", as used herein, is a stable mixture of at least two immiscible or partially immiscible liquids. In general, immiscible liquids tend to separate into two distinct phases. Accordingly, a surfactant may be added to stabilize the emulsion by reducing surface tension between the at least two immiscible or partially immiscible liquids and/or to stabilize the interface. For example, an emulsion may comprise a plurality of aqueous droplets in an immiscible oil, such as fluorocarbon oil, silicon oil or hydrocarbon oil (including, but not limited to, petroleum and mineral oil) where the droplet size ranges from about 0.5 to about 5000 microns in diameter.

In another embodiment, the samples to be tested are present in within a vehicle in a microfluidic device. A "microfluidic device", as used herein, is a device that enables a means of effecting a deterministic function on liquid or gas fluids at small scales typically measured in volumes such as, for example, milliliter (mL), microliter (µL), nanoliter (nL), picoliter (pL), or femtoliter (fL) volumes and/or by physical scale such as millimeter (mm), micrometer (µm) (also referred to as "micron"), nanometer (nm), picometer (pm), or femtoliter (fm). Functions may include mixing, splitting, sorting, heating, and so forth. Microfluidic devices may comprise microfluidic channels as a means for transferring fluids or samples from one point to another and are typically of uniform cross section in the mm, µm or nm scale.

In one embodiment of the present invention, a spectroscopic substance comprises one or more light-scattering molecule. A "light-scattering molecule", as used herein, means a molecule capable of propagating energy in the form of light that is scattered and comprises characteristic colors of light following illumination, for example but not limited to, by a broadband light source.

In another embodiment of the present invention, a spectroscopic substance comprises one or more chemiluminescent molecule. A "chemiluminescent molecule", as used herein, means a molecule capable of emitting light as chemiluminescence as a result of one or more chemical processes. Typical examples of chemiluminescent reactions involve the catalyzed formation of unstable organic peroxides, which emit single photons as they decay to lower-energy states. A common example of a chemiluminescent compound is luminol (CAS 521-31-3), which produces a chemiluminescent reaction in the presence of an oxidizer (for example, hydrogen peroxide catalyzed with potassium ferracyanide to form oxygen) and a hydroxide salt. Examples in the art of the diagnostic application of chemiluminescence include, but are not limited to, those in which the concentration of an enzyme, which acts as a catalyst to the chemiluminescent reaction, is to be measured, as with the use of luminol to detect hemoglobin, and those in which the chemiluminescent compound is labeled directly to a reagent, as in immunoassays employing chemiluminescent complementary binding partners. One of skill in the art will know and appreciate these and many other examples of chemiluminescent reactions in the art, including those described in, for example, K. and R. Van Dyke eds. 1990, *Luminescence Immunoassay and Molecular Applications*, Boca Raton: CRC Press.

In another embodiment of the present invention, a spectroscopic substance comprises one or more selectively absorbent molecule. A "selectively absorbent molecule", as used herein, is a molecule that absorbs certain characteristic colors or wavelengths of light while allowing other colors or wavelengths of light to pass or transmit through the molecule when a broadband light source is directed at the molecule. One of skill in the art will know and appreciate the numerous selectively absorbent molecules that may be used to comprise the selectively absorbent substance/constituent according to the present invention, including but not limited to, those commercially available from Exciton (Dayton, Ohio) and QCR Solutions, Corp. (Port St. Lucie, Fla.).

In another embodiment of the present invention, a spectroscopic substance comprises one or more fluorescent molecule. A "fluorescent molecule", as used herein, means a "fluorescent material" or "fluorescent label" or "fluorophore" or "fluorescent dye", each of which as used herein may be a fluorescent molecule, a fluorescent semiconductor nanoparticle (referred to as a "quantum dot"), or a chelated lanthanide or lanthanoid, having the ability to absorb energy from light of a specific wavelength, and then emit this energy as fluorescence having another specific wavelength characteristic for the particular molecule or quantum dot. In this manner, the fluorophore will facilitate the final assay readout indicating the presence or absence of a particular target of interest in the sample.

The particular fluorophore employed is not critical to the present invention. Fluorophores are known in the art and are described, for example, by Marras, "Selection of Fluorophore and Quencher Pairs for Fluorescent Nucleic Acid Hybridization Probes", In: V. Didenko, ed. 2006. *Fluorescent Energy Transfer Nucleic Acid Probes: Designs and Protocols* (Methods in Molecular Biology, vol. 335). New Jersey: Humana Press Inc., pp. 3-16. Examples of fluorophores that may be employed in the present invention include, but are not limited to, those described by Marras 2006 and further described herein below. One of skill in the art will appreciate the various fluorescent dyes that may serve as fluorescent molecules and that may be employed in the present invention and which are available from various commercial vendors.

Examples of fluorescent dyes that may be employed in the present invention include, but are not limited to, the following: fluorescein and derivatives thereof (e.g., fluorescein isothianate (FITC), carboxyfluorescein (FAM), tetrachlorofluorescein (TET), 2',7'-difluorofluorescein (Oregon Green® 488), Oregon Green® 514 carboxylic acid, and a fluorescein with chloro and methoxy substituents (JOE and 6-JOE)); rhodamine derivatives (e.g., tetramethyl rhodamine (TAMRA), tetramethyl rhodamine iso-thiocyanate (TRITC), tetramethylrhodamine (TMR), carboxy-X-rhodamine (ROX), Texas Red (a mixture of isomeric sulfonyl chlorides and sulforhodamine; Invitrogen™) and Texas Red-X (Texas Red succinimidyl ester, which contains an additional seven-atom aminohexanoyl spacer ("X") between the fluorophore and its reactive group; Invitrogen™), and Rhodamine X); cyanine (Cy) dyes (e.g., Cy3, Cy5 and Cy5.5) and cyanine derivatives (e.g., indocarbocyanine (Quasar® 570, Quasar® 670 and Quasar® 705), Oregon Green® isothiocyanate, and eosin isothiocyanate (EITC)); N-hydroxysuccinimidyl 1-pyrenebutyrate (PYB); N-hydroxysuccinimidyl 1-pyrenesulfonate (PYS); (5-(2'-aminoethyl)aminonaphthalene (EDANS); CAL Fluor® Gold 540, CAL Fluor® Orange 560, Fluor® Red 590, CAL Fluor® Red 610, and CAL Fluor® Red 635 (proprietary fluorophores available from Biosearch Technologies, Inc.); VIC®; HEX® (a 6-isomer phosphoramidite); and NED®.

The particular quantum dot (QD) employed is not critical to the present invention. Quantum dots are known in the art and are described, for example, by Han et al., "Quantum-dot-tagged Microbeads for Multiplexed Optical Coding of Biomolecules", *Nat Biotechnol* (July 2001) vol. 19, pp. 631-635. One of skill in the art will appreciate the various quantum dots that may serve as fluorescent labels and that can be employed in the present invention and which are available from various commercial vendors. Examples of quantum dots (QDs) that may be employed in the present invention include, but are not limited to, the following: cadmium selenide (CdSe) quantum dot nanoparticles (e.g., CdSe Quantum Dot Cores, 480-640 nm emission spectra, Sigma-Aldrich®); cadmium sulfide (CdS) quantum dot nanoparticles (e.g., CdS Quantum Dot Cores, 380-480 nm emission spectra, Sigma-Aldrich®); zinc sulfide-capped cadmium selenide (ZnS-capped CdSe) nanocrystals (e.g., CdSe/ZnS Lumidots™ and CdSe/ZnS NanoDots™, 480-640 nm emission spectra, Sigma-Aldrich®); and cadmium-free quantum dots (e.g., CFQD™, 400-650 nm emission spectra, Sigma-Aldrich®).

The particular chelated lanthanide or lanthanoid employed is not critical to the present invention. Lanthanides and lanthanoids are known in the art to comprise the fifteen metallic chemical elements with atomic numbers 57 through 71, from lanthanum (La) through lutetium (Lu). Examples of lanthanides or lanthanoids in chelated form that may be employed in the present invention include, but are not limited to, the following: lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu).

Dyes may be incorporated into a vehicle, such as a droplet, either at the time of droplet formation or after droplet formation using any injection method known and appreciated by one of skill in the art. Dyes may be incorporated during droplet formation by flowing or streaming the desired dye composition as a fluid stream into a droplet-maker design. Droplet-making designs and methods include but are not limited to those described in International Patent Publications WO 2004/002627 and WO 2006/096571, each of which is incorporated herein in its entirety.

According to the method of the present invention, the sample to be tested may be analyzed for spectroscopic intensity measurements of each spectroscopic substance, wherein the spectroscopic intensity measurement of the reference spectroscopic substance may be used to correct the spectroscopic intensity measurement of one or more sample spectroscopic substances. Depending on the application, the spectroscopic properties may comprise: light scattered from a sample to be tested following illumination of the sample to be tested; light emitted as chemiluminescence by a chemical process within the sample to be tested; light selectively absorbed by a sample to be tested following direction of a broadband light source at the sample to be tested; or light emitted as fluorescence from a sample to be tested following excitation of the sample to be tested.

The spectroscopic intensity and wavelength of a spectroscopic substance may be measured by any methods for spectroscopic analysis known and appreciated by one or ordinary skill in the art. Spectroscopic methods that may be utilized in the present invention include, but are not limited to, a laser and photodetector pair system or more complex optics known to those of skill in the art where the path of an optical beam intersects with the path of a spectroscopic substance and the excitation or illumination of the spectroscopic substance is captured by an optical path comprising one or more objective, mirror, and/or lens to direct the light to a photomultiplier tube (PMT) or photosensitive camera. A known fluoroscopy method that will be known and appreciated by one of skill in the art for use in the present invention is the use of flow cytometry instrumentation.

The reference spectroscopic substance should be chosen so as to have a signal that is distinguishable from the one or more sample spectroscopic substances. While the reference spectroscopic substance and the one or more sample spectroscopic substances may each comprise the same type of spectroscopic substance, it is impractical to select a reference spectroscopic substance that exactly matches the one or more sample spectroscopic substances in composition, as one cannot separate out the signal between two identical spectroscopic substances. The reference spectroscopic substance should inhabit substantially the same environmental conditions as those of one or more sample spectroscopic substances when spectroscopic intensity is measured. When practical, it is preferable that the reference spectroscopic substance be excited or illuminated by the same light source as the one or more sample spectroscopic substances, such that the reference spectroscopic substance can capture fluctuations in the power of the excitation or illumination light that may contribute to "noise" in the signal. For example, if the reference spectroscopic substance is excited or illuminated by light source A and at least one of the one or more sample spectroscopic substances is excited or illuminated by light source B, then variations in the reference spectroscopic substance may be attributed to light source A and may have no bearing on the variations due to light source B. A combination of different quantities and types of spectroscopic substances allows one to assign a unique value to and a more accurate determination of the spectroscopic intensity measured in each sample to be tested.

According to the method of the present invention, the samples to be tested are analyzed for spectroscopic intensity measurements of the reference spectroscopic substance and one or more sample spectroscopic substances, wherein the spectroscopic intensity measurement of the reference spectroscopic substance is used to correct the spectroscopic intensity measurements of the one or more sample spectroscopic substances. The intensities of both the reference spectroscopic substance and the one or more sample spectroscopic substances are measured and compared, resulting in a relatively precise measurement of the intensity of the one or more sample spectroscopic substances.

The spectroscopic intensity measurements may comprise one or more methods, including but not limited to, light scatter, absorption, chemiluminescence, fluorescent intensity, radiation decay counts, colorimetric, and so forth. Samples to be tested are placed in the path of an excitation energy source such as a light source selected from but is not limited to, lasers, light-emitting diodes (LEDs), arc lamps, broadband light source, and high intensity light bulbs. The spectroscopic substances in the sample to be tested scatter, absorb, chemiluminesce, or fluoresce (also referred to herein as "signal") in the form of light at a wavelength substantially different from the wavelength of the light source. This light from the sample to be tested is then captured by a detector or sensor, which may be selected from but is not limited to, a camera, a charge coupled device (CCD), a complementary metal-oxide-semiconductor (CMOS) (alternatively referred to as a complementary-symmetry metal-oxide-semiconductor (COS-MOS)), one or more individual photodiodes, photodiode arrays (PDAs), avalanche photodiodes (APDs), avalanche photodiodes arrays, photomultiplier tubes (PMTs), or photomultiplier tube arrays.

Known optical or electronic means may be optionally used to amplify the light from the light source and/or the light from the sample to be tested and/or to separate one or both into its component wavelengths. Selecting a reference spectroscopic substance and one or more sample spectroscopic substances for a particular sample to be tested such that each spectroscopic substance scatters light, selectively absorbs light, emits light in the form of chemiluminescence or fluorescence, depending upon the spectroscopic substance and particular application, at substantially different wavelengths allowing for easier separation of the respective wavelengths. The difference between the reference spectroscopic substance's expected value and measured value can be used to quantify the contribution of "noise" to the output, assuming the reference spectroscopic substance and the one or more sample spectroscopic substances are subject to the same measurement conditions (e.g., the power of the light source, detector or sensor noise, humidity, heat, pH of the sample to be tested, and the vehicle that the sample to be tested itself is in). The contribution of "noise" to the reference spectroscopic substance signal should correlate with the contribution of noise to the signal of the one or more sample spectroscopic substances. This correlation may be, and is typically, proportional but could vary linearly, exponentially, or in other manners or functions as well.

Figure 1:
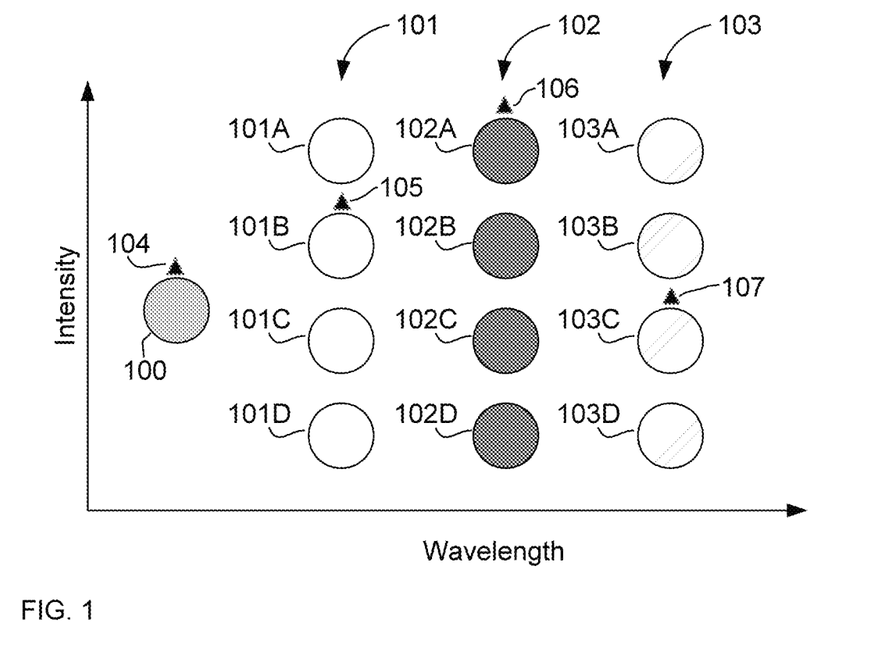
FIG. 1 illustrates an example of a reference spectroscopic substance comprising, by way of example, a fluorescent dye, in relation to three sample spectroscopic substances, each of which comprises, by way of example, a different fluorescent dye, wherein the combinations of different colors and concentrations of each fluorescent dye may be utilized for barcoding a sample to be tested.

Referring now to FIG. 1, which illustrates an example of a reference spectroscopic substance in relation to three sample spectroscopic substances, wherein each spectroscopic substances is a substantially distinct fluorescent dye, and wherein the combinations of different colors and intensities of each dye (referred to as "reference dye" and "sample dyes", respectively) may be utilized for barcoding a sample to be tested, according to the present invention. While the spectroscopic substances in this example are fluorescent dyes, any other spectroscopic substance may be used in this and any other example herein, as previously described.

In this example, a reference dye 100 is illustrated having known or standard intensity and wavelength. Additionally, three sample dyes 101-103 having specific wavelengths are illustrated, each exhibiting four (by way of example only as more or less numbers may be observed) clusters of intensities for each sample dye (101A-D, 102A-D, and 103A-D, respectively and representative of varying concentrations) at fixed respective wavelengths. Detection of all such wavelengths typically occurs at one instance, but may occur at different times.

As illustrated, barcode clusters of measurements for each dye are detected and illustrated as reference dye 100 (for which there is only a single cluster), sample dye 101 barcode clusters 101A-D, sample dye 102 barcode clusters 102A-D, and sample dye 103 barcode clusters 103A-D. Individual measurement event 104 clearly belongs to the reference dye (single cluster) 100 as there is only one cluster observed for the reference dye 100, however, it is initially unclear whether individual measurement event 105 of sample dye 101 belongs to sample dye 101 barcode cluster 101A or 101B, which illustrates how measurement shift for concentration changes affects all the wavelengths similarly. However, a similar shift in measurement event 104 from the center of reference dye (single cluster) 100 makes it clear that measurement event 105 corresponds to sample dye 101 barcode cluster 101B. In similar manner, measurement event 106 is not clearly inside of one of the clusters (102A-D) of sample dye 102. Applying the similar shift in measurement event 104 from the center of the reference dye (single cluster) 100 to that of measurement event 106 makes it clear that measurement event 106 corresponds to sample dye 102 barcode cluster 102A. Finally, measurement event 107 does not appear to be clearly inside of one of the clusters (103A-D) of sample dye 103, but applying the similar shift in measurement event 104 from the center of the reference dye (single cluster) 100 to that of measurement event 107 makes it clear that measurement event 107 corresponds to barcode cluster 103C of sample dye 103.

Figure 2A:
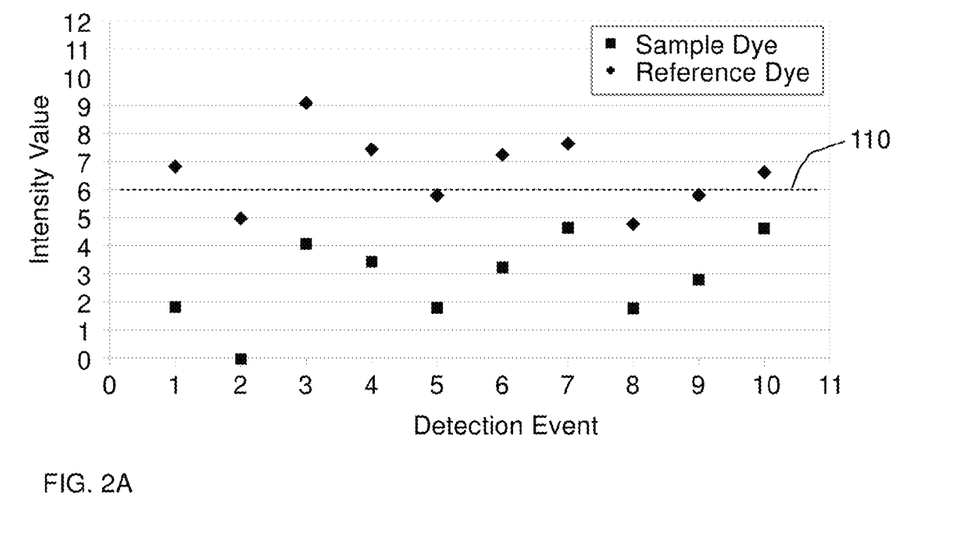
FIGS. 2A-C are diagrams illustrating an example of one embodiment of a method of using a reference spectroscopic substance to correct for the measured signals of a sample spectroscopic substance, wherein each spectroscopic substance comprises, in this example, distinct fluorescent molecules.
Figure 2B:
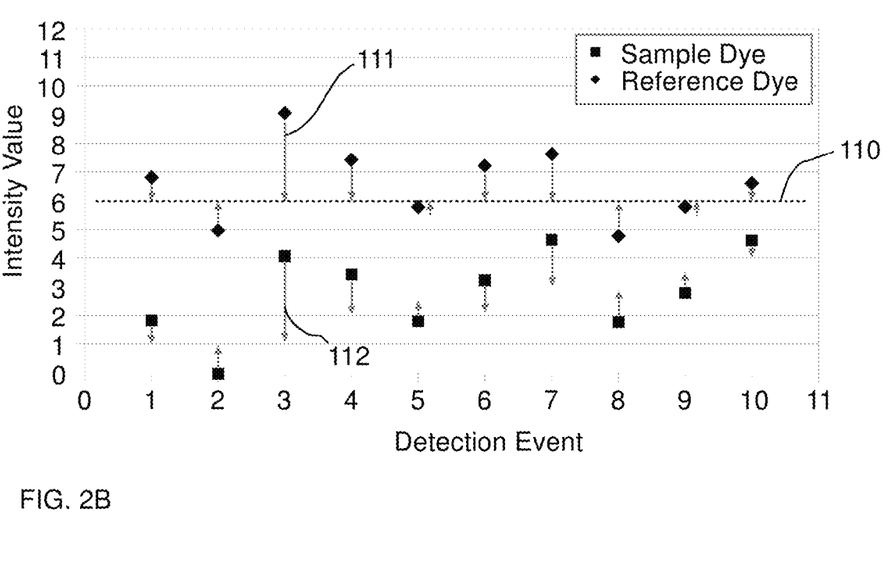
Figure 2C:
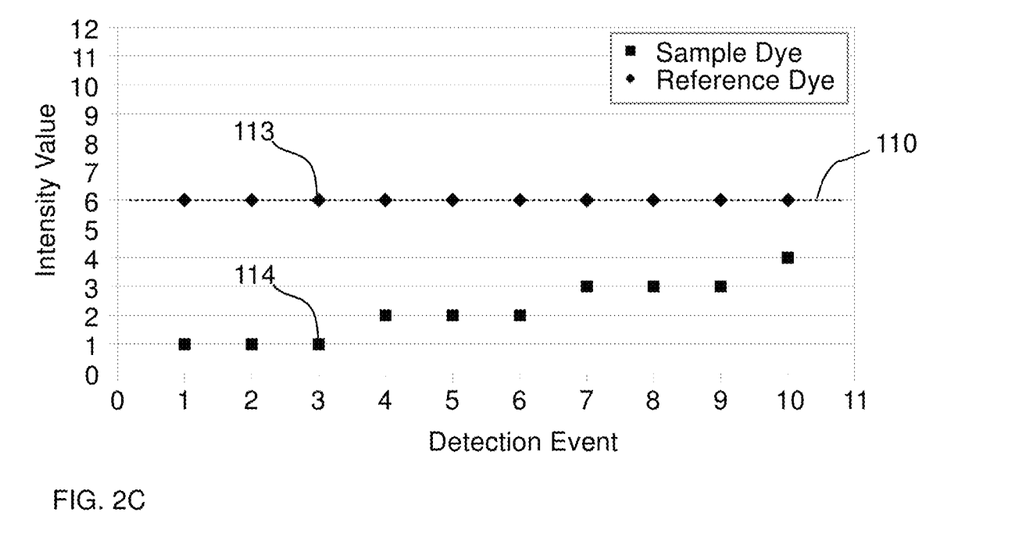

Referring now to FIGS. 2A-C, which are diagrams illustrating an example of one embodiment of a method of using a reference spectroscopic substance (a fluorescent dye, specifically Rhodamine-based dye called TAMRA dye (emission at 575 nm) referred to as "reference dye" in this example") used to correct for the measured signals of a sample spectroscopic substance (a fluorescent dye, specifically Fluorescein dye (emission at 525 nm) referred to as "sample dye" in this example), according to the present invention. In this example, 10 samples to be tested comprising different concentrations of the sample dye, together with the reference dye present at the same known concentration in each sample to be tested and having a known and expected intensity value of 6. The 10 samples to be tested were measured by flow cytometry utilizing a laser to excite the dye in each droplet, one by one, and then measuring the emitted fluorescence intensities using a PMT or similar detector. In this example, the concentration of the reference dye in each sample to be tested is the same known concentration and has been calibrated previously with the detector being used, such that the expected fluorescence intensity value of the reference dye in each sample to be tested is an intensity value of 6 in this example (with arbitrary units). This expected intensity value of 6 for the reference dye in each sample to be tested is illustrated by the horizontal dotted line 110 in FIGS. 2A-C.

FIG. 2A illustrates a plot of the measured intensity values of the reference dye and corresponding intensity values of the sample dye as detected and measured from the 10 different individual samples to be tested. Due to the use of a laser with quite a bit of fluctuation in its power output, as well as other possible environmental conditions that may contribute to noise or variation, some of the samples to be tested were excited with a much lower energy laser beam or much higher energy laser beam than desired. This variation manifests itself in the variable emission intensity values of the sample dye and reference dye as shown in FIG. 2A. As can be seen by the measured intensity value of the reference dye in each of the 10 droplets, while some are along the line of expected intensity value (110) some measured values are below or above that line.

FIG. 2B illustrates the determination of the difference between the expected and measured intensity values of the reference dye (designated as element 111 for droplet 3 by way of example) using the expected value of the reference dye (dotted line 110), as we assume this difference is dependent upon the variable energy strength of the exciting laser, we can determine the ratio of the difference between the expected and measured value of the reference dye (111) and apply the same ratio of difference to correct the readings of the sample dye (112). FIG. 2C illustrates the scaling used to correct the detected reference dye values applied to the sample dye measurements, resulting in corrected values 113 and 114 for the reference dye and sample dye, respectively in sample to be tested 3. The result is a plot illustrating sample dye values increasing in an approximately stepwise manner from sample to be tested 1 through sample to be tested 10.

Another embodiment of the present invention pertains to a method for managing variation in spectroscopic intensity measurements through the use of a reference component comprising a reference spectroscopic substance, wherein the reference spectroscopic substance is contained within a sample to be tested together with a sample of interest, and wherein the sample of interest comprises a nucleic acid sequence, referred to herein as a "sample nucleic acid", as in nucleic acid sequencing, and one or more sample spectroscopic substances. The sample nucleic acid may be obtained from a human, animal, plant, or microorganism and includes, but is not limited to, genomic or mitochondrial DNA or RNA, PCR amplicon, cDNA, and others. The sample nucleic acid may be double stranded or single stranded. In one example, the single stranded sample nucleic acid is DNA. In another example, a double stranded sample nucleic acid is first converted to a single stranded sample nucleic acid.

In one aspect of this embodiment, a single nucleotide within the sample nucleic acid sequence is detected. In another aspect of this embodiment, a particular locus may be queried to detect the presence or absence of a particular nucleic acid sequence variance. A "variance" is a difference in the nucleotide sequence among related polynucleotides. The difference may be the deletion of one or more nucleotides from the sequence of one polynucleotide compared to the sequence of a related polynucleotide, the addition of one or more nucleotides or the substitution of one nucleotide for another. The terms "mutation," "polymorphism" and "variance" are used interchangeably herein. As used herein, the term "variance" in the singular is to be construed to include multiple variances, i.e., two or more nucleotide additions, deletions and/or substitutions in the same polynucleotide. A "point mutation" refers to a single substitution of one nucleotide for another.

For example, a particular locus may be queried to detect the presence or absence of a single nucleotide polymorphism. A "single nucleotide polymorphism" or "SNP" refers to a variation in the nucleotide sequence of a polynucleotide that differs from another polynucleotide by a single nucleotide difference. A SNP included, for example and without limitation, exchanging one A for one C, G or T, or one C for one G, T or C and so on, in the entire sequence of polynucleotide. Additionally, it is possible to have more than one SNP in a particular nucleic acid sequence. For example, at one position in a nucleic acid sequence, a G may be exchanged for an A, at another position a C may be exchanged for a T and so on.

In another example, a particular locus may be queried to detect the presence or absence of a single nucleotide mutation. In another embodiment, a plurality of nucleotide targets (e.g., two or more nucleotides) is detected within the same reaction. In one aspect of this embodiment, a short nucleic acid sequence within the target nucleic acid sequence in detected. In one example, the nucleic acid probe is as short as about 6 to 8 nucleotides long. In another aspect of this embodiment, a full complement of short nucleic acid probes can be used sequentially to determine the entire sequence of the target nucleic acid. For example, the full complement of short nucleic acid probes may be a set of all 4096 possible hexamers. Accordingly, a target nucleic acid may be detected using the methods of this invention with no specific target length limitation.

Another embodiment of the present invention pertains to a method for managing variation in spectroscopic intensity measurements through the use of a reference component as previously described, further comprising a library of samples to be tested, wherein the reference spectroscopic substance and the one or more sample spectroscopic substances are substantially distinct when present within the same sample to be tested and, accordingly, each sample to be tested is uniquely identified by the combination of different colors and concentrations of spectroscopic substances comprised therein. In one aspect of this embodiment, the library of samples to be tested may be analyzed for spectroscopic intensity measurements of each spectroscopic substance, wherein the spectroscopic intensity measurement of the reference spectroscopic substance may be used to correct the spectroscopic intensity measurement of the one or more sample spectroscopic substances. In another embodiment of the method of the present invention, the library of samples to be tested may be present within a microfluidic device.

Another embodiment of the present invention pertains to a method for reducing the variation in spectroscopic intensity measurements in a library of samples to be tested through the use of a reference component as previously described, wherein each sample to be tested in the library of samples to be tested further comprises one or more probes, wherein each probe may comprise a DNA sequence, wherein each spectroscopic substance of the one or more sample spectroscopic substances serves as a unique identifier for the identity of a particular probe within a particular sample to be tested, and wherein the reference spectroscopic substance and the one or more sample spectroscopic substances within a particular sample to be tested are substantially distinct. In one aspect of this embodiment, each of the one or more probes may be substantially identical to each other when present within a single sample to be tested.

In this embodiment, each sample to be tested is uniquely identified by the combination of different colors and concentrations of spectroscopic substances comprised therein. In another aspect, each of the one or more probes may be substantially different from each other when present in separate samples to be tested. In one aspect of this embodiment, the library of samples to be tested may be analyzed for spectroscopic intensity measurements of each spectroscopic substance, wherein the spectroscopic intensity measurement of the reference spectroscopic substance may be used to correct the spectroscopic intensity measurement of the one or more sample spectroscopic substances. In another aspect, the identity of the one or more probes in each sample to be tested may be determined from the corrected spectroscopic intensity measurements of each sample spectroscopic substance. In another embodiment of the method of the present invention, the library of samples to be tested may be present within a microfluidic device.

Another embodiment of the present invention pertains to a method for managing variation in spectroscopic intensity measurements through the use of a reference component as previously described, further comprising an assay performed within a sample to be tested, and wherein the measured spectroscopic intensity may comprise a combination of the result(s) of the assay performed and the combination and concentration of spectroscopic substances within the sample to be tested. In one aspect of this embodiment, the concentration of the spectroscopic substances in the sample to be tested may be a result of adding the spectroscopic substances together, wherein the product of such addition may have variability that may result in undesired concentration variation. In another embodiment of the method of the present invention, the sample to be tested may be present within a microfluidic device.

The sample spectroscopic substance may be linked to the product of the reaction by any means known and appreciated by one of skill in the art including, but not limited to, chemical and physical interactions. For example, the product of the reaction may cause, either directly or through an enzymatic cascade, the cleaving or changing of the chemical bonds or structure of a spectroscopic substance resulting in a change in the intensity and/or wavelength of the emission of that spectroscopic substance. In another example, the one or more sample spectroscopic substances may be co-localized in physical proximity with an interacting spectroscopic substance that acts as a "quencher" to absorb the energy and emission signal of the one or more sample spectroscopic substances. The product of the reaction would remove the physical proximity between the interacting spectroscopic substance and the one or more sample spectroscopic substances, and thus changing the intensity of the emission of the sample spectroscopic substance. In order to compare the amount of product produced among the different samples to be tested, the spectroscopic intensities of the spectroscopic substances are used. For example, in embodiments employing fluorescent spectroscopic substances, fluorescent intensity readings may be impacted by fluctuation in the power output of the light source used to excite the fluorescent spectroscopic substances (dyes). Thus, as readings are taken over time, dyes in one or more samples to be tested may, by way of example, be excited by a light power of 110% while dyes in one or more other samples to be tested may be excited by a light power of 90%. In order to compare measurements of dyes taken under different light power conditions, a reference dye is used in each sample to be tested as a point of comparison to quantify the fluctuation in light power and correct the sample dye fluorescent intensity measurements.

In one aspect of any of the embodiments of the present invention, it may be desired to inject one or more substantially controlled volumes of fluid and/or emulsion into or out of a sample to be tested, particularly when the sample to be tested is in a droplet, as a way to introduce a new element to the reaction, wherein the volume comprises one or more reagents, substrates or other reaction components. The volumes injected into or out of a droplet may further comprise one or more reagents, reaction components or samples of interest selected from cells (including any eukaryotic or prokaryotic cells, including but not limited to cells selected from humans, animals, plants, fungi, bacteria, viruses, protozoa, yeasts, molds, algae, *rickettsia*, and prions); proteins, peptides, nucleic acid sequences, oligonucleotide probes, polymerase enzymes, buffers, dNTPs, organic and inorganic chemicals, and fluorescent dyes. The injected volumes include, but are not limited to, milliliter (mL), microliter (µL), nanoliter (nL), picoliter (pL), or femtoliter (fL) volumes. Injection of fluid and/or emulsion into or out of a droplet produces a droplet having a concentration of original contents that is relatively dilute or concentrated compared to the concentration prior to injection of fluid and/or emulsion into or out of the droplet. This results in relatively small variations in the volume among droplets within the library of droplets and, in particular, variations in the concentration of one or more sample spectroscopic substances. Thus, the spectroscopic intensity readings of the one or more sample substances are impacted by such variations. In order to compare measurements of droplets having different sample spectroscopic substance concentrations, a reference spectroscopic substance is utilized in each droplet as a point of comparison to quantify the amount of dilution or concentration and to correct the sample spectroscopic substances intensity measurements, as described previously.

The present invention also pertains to a kit containing the reagents necessary for performing a method for managing the variation in spectroscopic intensity measurements through the use of a reference component, according to the methods of the invention described previously.

The results of the methods and kits of this invention, referred to herein as "data", then be kept in an accessible database, and may or may not be associated with other data from that particular sample or with data from other samples. Data obtained may be stored in a database that can be integrated or associated with and/or cross-matched to other databases.

The methods and kits of this invention may further be associated with a network interface. The term "network interface" is defined herein to include any person or computer system capable of accessing data, depositing data, combining data, analyzing data, searching data, transmitting data or storing data. The term is broadly defined to be a person analyzing the data, the electronic hardware and software systems used in the analysis, the databases storing the data analysis, and any storage media capable of storing the data. Non-limiting examples of network interfaces include people, automated laboratory equipment, computers and computer networks, data storage devices such as, but not limited to, disks, hard drives or memory chips.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

FIGS. 3A-D illustrate data obtained from performance of one embodiment of a method for managing the variation in spectroscopic intensity measurements through the use of a reference component, according to the present invention. In this example, each sample to be tested is present within a vehicle, which is a droplet in this example, wherein each droplet was tested after injection of volume into each droplet, and wherein the variability of injection volumes resulted in variation among the spectroscopic intensity measurements obtained for each droplet. While a droplet is the vehicle utilized in this example, any other vehicle may be used in this and any other example or embodiment herein, as previously described.

In this example, a library of samples to be tested was prepared with each sample to be tested comprising a reference component comprising a reference spectroscopic substance (comprising a fluorescent molecule referred to as a "reference dye" in this example), together with a sample of interest comprising two sample spectroscopic substances (comprising fluorescent molecules, referred to as Dye 1 and Dye 2), wherein each sample to be tested is present within a droplet. The resulting barcoded droplets, with each droplet comprising a reference dye, one of four different concentrations of Dye 1, and one of five different concentrations of Dye 2, producing a total of 5×4=20 different barcode labels (barcoded droplets) to be tested. While the spectroscopic substances in this example are fluorescent dyes, any other spectroscopic substance may be used in this and any other example herein, as previously described.

Figure 3A:
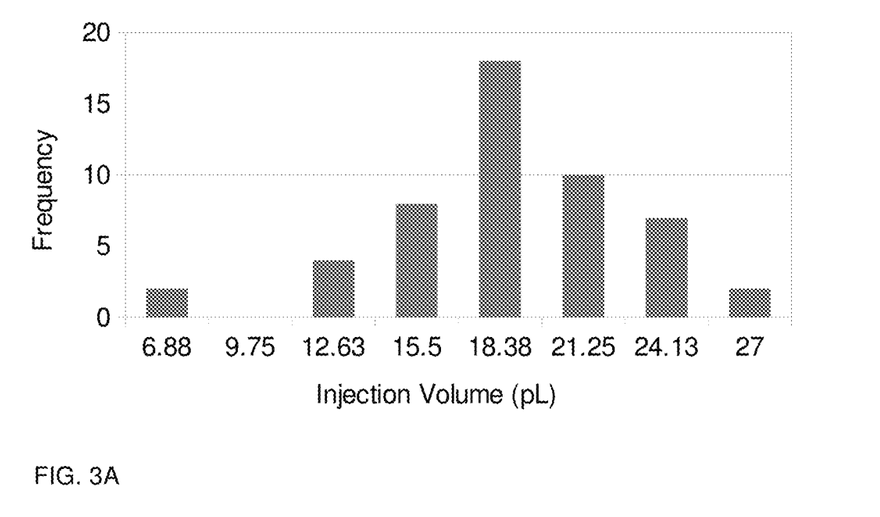
FIG. 3A illustrates a histogram distribution of injection volumes, wherein the variability of injection volumes may cause the droplet barcodes to vary from their expected values.

FIG. 3A illustrates a histogram of injection volumes, wherein the variability of injection volumes may cause the barcoded droplets to vary from their expected spectroscopic intensity values, as the dyes in each droplet may be either over diluted (less concentrated) or under diluted (more concentrated), directly affecting their respective measured intensities. After injection of all dyes, the fluorescence intensity of the droplets was measured and approximately 1000 droplets per barcode label were analyzed.

Figure 3B:
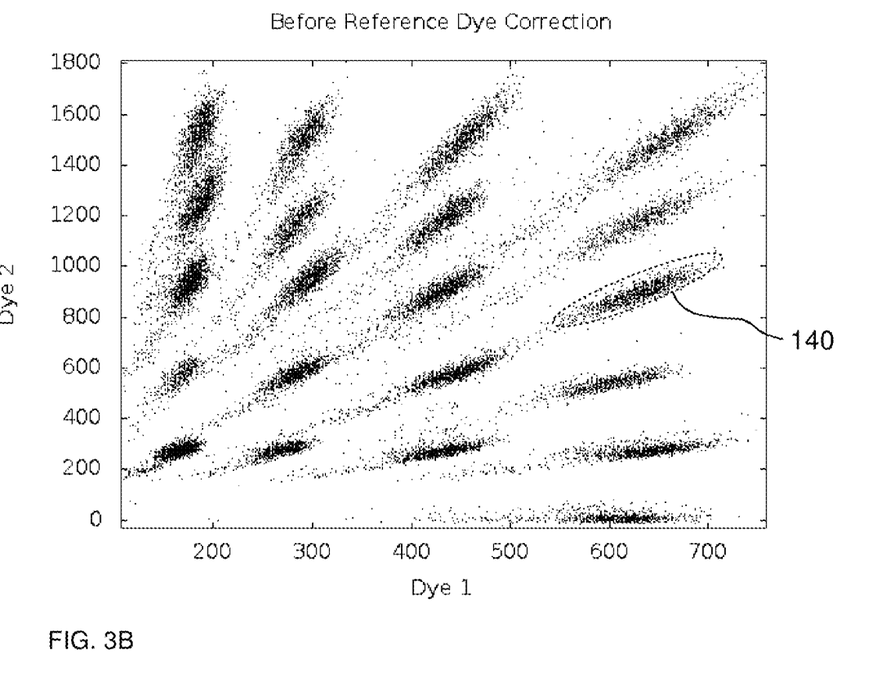
FIG. 3B shows the fluorescence intensity measurements of two sample spectroscopic substances, each of which comprises a distinct fluorescent dye, prior to correction with the reference spectroscopic substance, according to the method of the present invention.
Figure 3C:
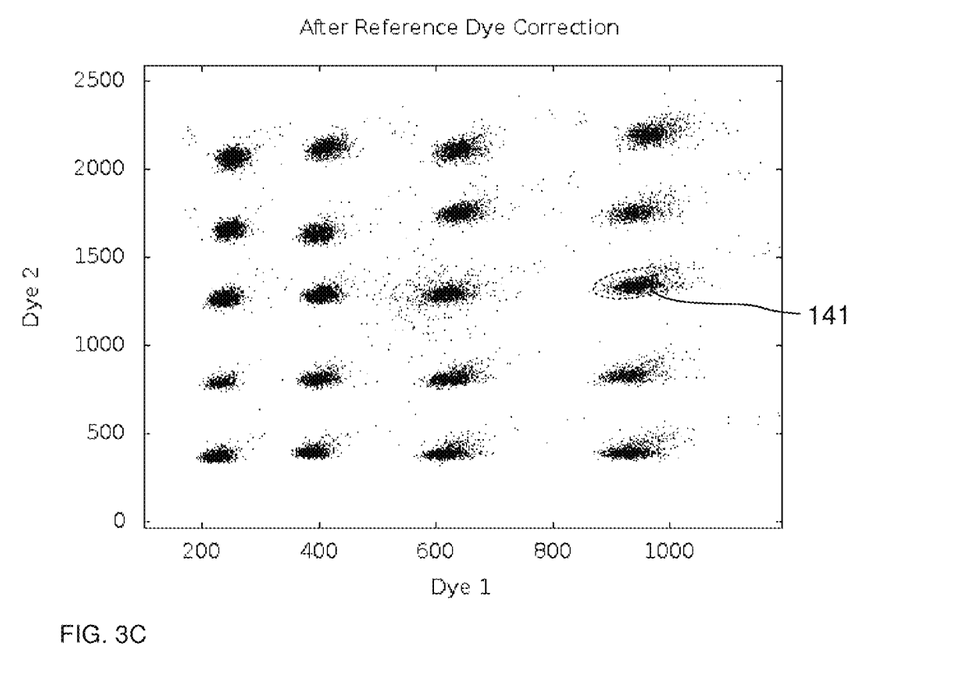
FIG. 3C shows the fluorescence intensity measurements of two sample spectroscopic substances after correction of the measured variation in intensity with a reference spectroscopic substance, according to the method of the present invention.
Figure 3D:
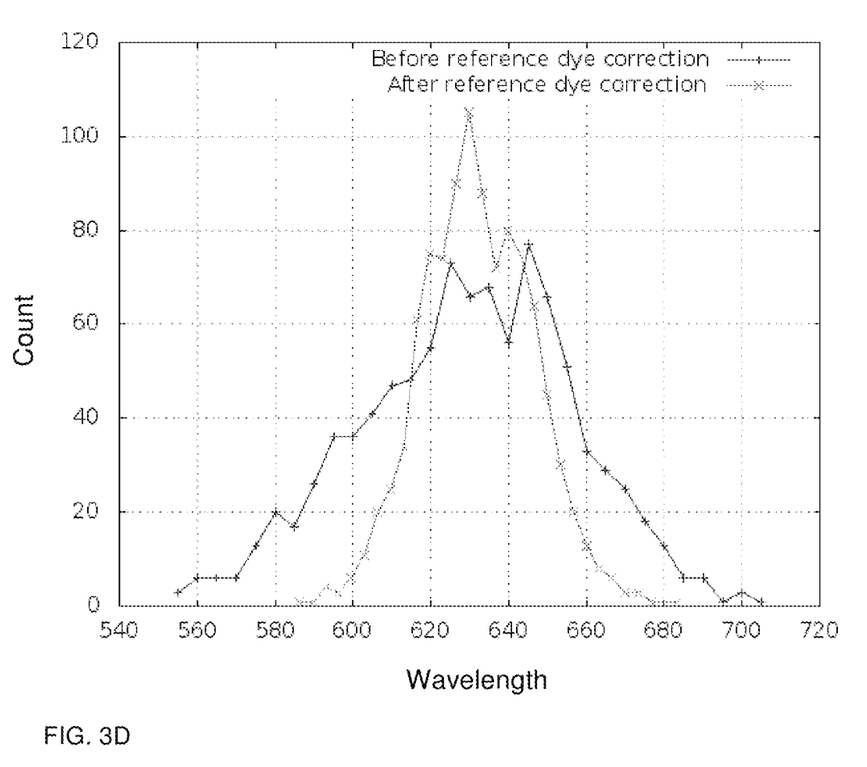
FIG. 3D shows the intensity distribution of one sample spectroscopic substance before and after reference spectroscopic substance correction, illustrating corrected measured intensity variation according to the present invention.

The clusters corresponding to the measurement of many droplets of the same dye combination levels are widely spread, as shown in FIG. 3B. FIG. 3B shows the fluorescence intensity measurements of Dye 1 and Dye 2 prior to correction with the reference dye. It is observed that clusters in FIG. 3B are widely spread and running into each other. An example of one cluster of measurements obtained from many droplets comprising the same combination of reference dye and sample dyes is highlighted as cluster 140, which demonstrates a relatively large spread of intensity values within a cluster of droplets. FIG. 3C shows the fluorescence intensity measurements of Dye 1 and Dye 2 in the previous cluster 140, now designated as cluster 141 and exhibiting relatively tighter (i.e., smaller) spread of intensity values within the cluster 141, after correction with a reference dye. FIG. 3D shows the intensity distribution of Dye 1 for one cluster of droplets both before and after reference dye correction, illustrating a decrease in fluorescence intensity variation after correction. This correction has effectively removed the variation in volumes introduced by the initial injection step.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A library of samples in droplets in an emulsion, wherein each droplet comprises:
   a reference component comprising a fluorescent reference spectroscopic substance, wherein each droplet contains the same reference component,
   a sample comprising a molecule of interest, wherein the molecule of interest is one or more oligonucleotide probe; and
   one or more sample fluorescent spectroscopic substances, wherein a combination of intensity of sample fluorescent spectroscopic substances and identity of sample fluorescent spectroscopic substances provides a barcode to identify the one or more oligonucleotide probe;
   wherein the reference spectroscopic substance and the one or more sample spectroscopic substances are uniquely identifiable, and wherein the library of samples comprises three sample fluorescent spectroscopic substances.

2. The library of claim 1, wherein the droplets are present within a microfluidic device.

3. The library of claim 1, wherein each of the one or more oligonucleotide probes is identical to each other when present within the same droplet.

4. The library of claim 1, wherein each of the one or more oligonucleotide probes is different from each other when present within different droplets.

5. The library of claim 1, wherein the droplets each comprise two sample fluorescent spectroscopic substances.

6. The library of claim 1, wherein the droplets each comprise three sample fluorescent spectroscopic substances.

7. The library of claim 1, wherein there are variations in concentration of the one or more sample fluorescent spectroscopic substances between droplets.

8. The library of claim 1, wherein the reference fluorescent spectroscopic substance is at the same concentration across different droplets.

9. A system comprising:
a laser;
a photodetector; and
the library of claim 1.

* * * * *